United States Patent [19]
Havinga et al.

[11] 3,933,903
[45] Jan. 20, 1976

[54] PROCESS FOR THE PREPARATION OF CYCLOALKYLALKANE CARBOXYLIC ACID

[75] Inventors: Reginoldus Havinga, Schalkhaar; Antoon Wildschut, Bathmen, both of Netherlands

[73] Assignee: Akzo N.V., Arnhem, Netherlands

[22] Filed: June 3, 1974

[21] Appl. No.: 475,875

[30] Foreign Application Priority Data
June 12, 1973  Netherlands.................... 7308108

[52] U.S. Cl........................... 260/514 R; 260/514 H
[51] Int. Cl.$^2$......................................... C07C 61/38
[58] Field of Search............................... 260/514 R

[56] References Cited
OTHER PUBLICATIONS
C & E. News, "Ketons Cleared at Room Temperature" Apr. 20, 1964.

Primary Examiner—Anton H. Sutto
Attorney, Agent, or Firm—Stevens, Davis, Miller & Mosher

[57] ABSTRACT

A process is disclosed for effectively producing a cycloalkylalkane carboxylic acid by reacting a cyclic ketone or a cyclic alcohol with a molten alkali metal hydroxide using a two step temperature treatment during the reaction wherein the first step temperature ranges from 200° to 270°C and the second step temperature ranges from 290° to 350°C. The alkali metal soap is then converted to the free acid. The process is especially directed to the manufacture of cyclopentylpropionic acid.

8 Claims, No Drawings

PROCESS FOR THE PREPARATION OF CYCLOALKYLALKANE CARBOXYLIC ACID

The present invention relates to a process for the preparation of a cycloalkylalkane carboxylic acid by reacting a cyclic ketone or a cyclic alcohol with a molten alkali metal hydroxide.

It is known that alcohols and ketones can be converted into carboxylic acid soaps with molten caustic soda. For example, in U.S. Pat. No. 3,121,728 there is described the preparation of caproic acid by reacting cyclohexanol with molten caustic soda. However, U.S. Pat. No. 1,961,623 shows that the oxidation of cyclohexanol or cyclohexanone with a molten alkali metal hydroxide does not lead to a distinct product, but rather to a mixture of caproic acid, cyclohexylbutyric acid and a higher carboxylic acid having the empirical formula $C_{12}H_{20}O_{21}$, the latter acid being identified in *J. Am. Chem. Soc.*, 72, (1950) 2039 as 6-(2-cyclohexenyl) caproic acid. According to the latter patent, this cyclohexenylcaproic acid, after having been isolated, can be converted into cyclohexylbutyric acid by reaction with molten alkali metal hydroxide.

Consequently, it is not attractive to prepare cyclohexylbutyric acid by means of a caustic soda melt reaction from cyclohexanol or cyclohexanone, as the yield of the desired cyclohexylbutyric acid is low due to by-product formation. As improvement in this yield can only be obtained by isolating the cyclohexenylcaproic acid formed as an intermediate and then converting same into cyclohexylbutyric acid.

Surprisingly it has now been found that starting from cyclopentanone or cyclopentanol, cyclopentylpropionic acid may be obtained in good yields by reacting cyclopentanone or cyclopentanol with molten alkali metal hydroxide in two successive heating steps at temperatures ranging from 200° to 270°C and from 290° to 350°C respectively and subsequently converting the alkali metal soap formed into the cyclopentylpropionic acid in a conventional manner by acidifying the reaction mixture with a mineral acid.

Potassium hydroxide or an alkali metal hydroxide consisting essentially of potassium hydroxide is preferably used as the alkali metal hydroxide. The first heating step is preferably carried out at a temperature ranging from 240° to 260°C.

In order to improve the stirrability of the reaction mixture, the oxidation of the ketone or the alcohol is preferably carried out in the presence of an alkali metal soap of a different alkane carboxylic acid, such as, for example, diethyl acetic acid, 2-ethylhexanoic acid and 3,5,5-trimethylhexanoic acid, preferably isobutyric acid. These metal soaps may be formed in situ, if desired. They are added or formed in quantities ranging from 5 to 50 mol %, calculated on the total quantity of base.

The cyclopentylpropionic acid prepared according to the process of the invention may be used in its ester form in the cosmetic or pharmaceutical industry. The following Examples I to III illustrate the process of the invention, Examples IV and V being given for comparative purposes only.

EXAMPLE I

To 77.5 g (0.92 mol) of cyclopentanone were added, with stirring, a mixture of 33 g of 98% by weight NaOH, 99 g of 85% by weight KOH (totally 2.30 mol of base) and 61 g (0.69 mol) of isobutyric acid at a temperature of 220°C over a period of 1 hour.

After all the cyclopentanone had been added, the temperature of the reaction mixture was raised to 315°C and kept at this temperature until no more hydrogen was formed.

After cooling, the melt was diluted with about 0.5 l of water and acidified with 200 ml of 36% by weight HCl (2.40 mol). After separation the organic layer was washed with water and fractionally distilled, after which 39.4 g of 3-cyclopentylpropionic acid were obtained (yield 60.2%).

EXAMPLE II

To 1008 g of (12 mol) of cyclopentanone were added a mixture of 548 g of 97% by weight NaOH, 1096 g of 85% by weight KOH (totally 30 mol of base) and 792 g (9 mol) of isobutyric acid at a temperature of 250°C for 1 hour.

After all the cyclopentanone had been added, the temperature of the reaction mixture was raised to 310° – 315°C and kept at this temperature until no more hydrogen was formed.

After cooling, the melt was diluted with 4 l of water and acidified with 2.6 l of 36% by weight HCL (31 mol). After separating, the organic layer was washed with water and distilled fractionally to give 631 g of 3-cyclopentylpropionic acid (yield 74.0%).

EXAMPLE III

To 1008 g of (12 mol) of cyclopentanone were added a mixture of 1980 g of 85% by weight KOH (30 mol) and 792 g (9 mol) of isobutyric acid at a temperature of 250°C over 1 hour.

After all the cyclopentanone had been added, the temperature of the reaction mixture was raised to 305°–310°C and kept at this temperature until no more hydrogen was formed.

In order to isolate the acid desired, the melt was worked up in the manner described in Example II giving 675 g of 3-cyclopentylpropionic acid (yield 79.2%). In a similar way, 3-cyclopentylpropionic acid was obtained from cyclopentanol in a yield of 72%.

COMPARATIVE EXAMPLES

EXAMPLE IV

To 82 g (0.98 mol) of cyclopentanone were added a mixture of 60 g of 85% by weight KOH, 20 g of 98% by weight NaOH (totally 1.40 mol of base) and 37 g (0.42 mol) of isobutyric acid at a temperature of 310°C over a 1 hour period.

Immediately thereafter the melt was diluted with about 0.5 l of water and acidified with 125 ml of 36% by weight HCl (1.50 mol). After separating, the organic layer was washed with water and distilled fractionally to give 12.4 g of 3-cyclopentylpropionic acid (yield 17.8%).

EXAMPLE V

To 73.5 g (0.87$^5$ mol) of cyclopentanone were added a mixture of 84 g of 98% by weight NaOH, 84 g of 85% by weight KOH (totally 3.33 mol of base) and 40.69 g (0.35 mol) of diethylacetic acid at a temperature of 340°C for 1 hour.

Immediately thereafter, the melt was diluted with about 1 l of water and acidified with 300 ml of 36% by weight HC1 (3.60 mol). After separating, the organic layer was washed with water and distilled fractionally.

3-Cyclopentylpropionic acid in an amount of 8.6 g was obtained (yield 13.8%). What is claimed is:

1. A process for preparing cyclopentylpropionic acid comprising reacting cyclopentanone or cyclopentanol with molten alkali metal hydroxide in two successive heating steps at temperatures ranging from 200° to 270°C and from 290° to 350°C respectively and subsequently converting the alkali metal soap of cyclopentylpropionic acid formed into the free acid.

2. The process of claim 1 wherein the first heating step is carried out at a temperature ranging from 240° to 260°C.

3. The process of claim 1 wherein said alkali metal hydroxide is predominantly potassium hydroxide.

4. The process of claim 1 wherein the reaction is carried out in the presence of an alkali metal soap of an acid different from cyclopentylpropionic acid.

5. The process of claim 4, wherein the reaction is carried out in the presence of isobutyric acid.

6. The process of claim 4 wherein said alkali metal soap is formed in situ.

7. A process for preparing cyclopentylpropionic acid comprising reacting cyclopentanone or cyclopentanol with molten potassium or sodium hydroxide or a mixture of said hydroxides in two successive heating steps at a temperature ranging from 200° 270°C. and from 290° to 350°C., respectively, and subsequently converting the metal soap of cyclopentylpropionic acid formed into the free acid.

8. A process for preparing cyclopentylpropionic acid comprising reacting cyclopentanone or cyclopentanol with molten potassium or sodium hydroxide or mixture of said hydroxides in two successive heating steps at a temperature ranging from 200° to 270°C. and from 290° to 350°C., respectively, in the presence of isobutyric acid or diethylacetic acid and subsequently converting the alkali metal soap of cyclopentylpropionic acid formed into the free acid.

* * * * *